United States Patent [19]

Hoefle et al.

[11] Patent Number: 4,824,843

[45] Date of Patent: Apr. 25, 1989

[54] SUBSTITUTED AMIDE INHIBITORS OF CHOLESTEROL ABSORPTION

[75] Inventors: Milton L. Hoefle; Robert F. Meyer, both of Ann Arbor, Mich.

[73] Assignee: Warner-Lambert Company, Morris Plains, N.J.

[21] Appl. No.: 66,688

[22] Filed: Jun. 25, 1987

[51] Int. Cl.$^4$ .................. A61K 31/42; A61K 31/535; C07D 263/14; C07D 265/08

[52] U.S. Cl. .................. 514/228.8; 514/364; 514/374; 514/508; 514/88; 548/136; 548/236; 548/237; 558/6

[58] Field of Search .................. 544/88; 548/136, 236, 548/237; 558/6; 514/228.8, 364, 374, 508

[56] References Cited

U.S. PATENT DOCUMENTS 4,413,011 11/1983 Sircar .................. 424/309
4,465,507 8/1984 Konno .................. 71/98
4,554,282 11/1985 Sircar .................. 424/309

FOREIGN PATENT DOCUMENTS 1064252 4/1967 United Kingdom .

OTHER PUBLICATIONS

Kritchevsky, D. et al., *Lipids*, vol. 12, pp. 16–21 (1977).
Heider, J. G. et al., *Journal of Lipid Research*, vol. 24, pp. 1127–1134 (1983).
Clark, S. B. and Tercyak, A. M., *Journal of Lipid Research*, vol. 25, pp. 148–159 (1984).

*Primary Examiner*—Richard L. Raymond
*Attorney, Agent, or Firm*—Francis J. Tinney

[57] ABSTRACT

Novel N-(substituted-phenyl)-5-(2,5-dimethylphenoxy)-2,2-dimethylpentanamides which are useful in preventing the intestinal absorption of cholesterol, as well as novel pharmaceutical compositions and methods of use, as well as processes for their manufacture are herein described.

25 Claims, No Drawings

SUBSTITUTED AMIDE INHIBITORS OF CHOLESTEROL ABSORPTION

BACKGROUND OF THE INVENTION

The present invention relates to novel substituted amides useful as pharmaceutical agents, to methods for their production, to pharmaceutical compositions which include these compounds and a pharmaceutically acceptable carrier, and to a pharmaceutical method of treatment. More particularly, the novel compounds of the present invention prevent the intestinal absorption of cholesterol in mammals by inhibiting acyl-coenzyme A: cholesterol acyltransferase (ACAT).

The atheromatous plaque, which is the characteristic lesion of atherosclerosis, results from deposition of plasma lipids, mainly cholesteryl esters, in the intima of the arterial wall. Progressive enlargement of the plaque leads to arterial constriction and ultimately coronary heart disease. A number of clinical trials have shown a causal relationship between hypercholesterolemia and coronary heart disease.

Agents that control dietary cholesterol absorption moderate serum cholesterol levels. Dietary cholesterol is absorbed from the intestinal lumen as free cholesterol which must be esterified with fatty acids. This reaction is catalyzed by the enzyme acyl-CoA: cholesterol acyltransferase (ACAT). The resulting cholesteryl esters are packaged into the chylomicrons which are secreted into the lymph. Inhibitors of ACAT not only prevent absorption of dietary cholesterol but also prevent the reabsorption of cholesterol which has been released into the intestine through endogenous regulatory mechanisms, thus lowering serum cholesterol levels and ultimately counteracting the formation or development of atherosclerosis.

British Pat. No. 1,064,252 to Waring, W. S., Published Apr. 5, 1967; U.S. Pat. No. 3,708,514 to Murakami, M., et al., issued Jan. 2, 1973; Kritchevsky, D., et al., *Lipids*, Vol 12, p. 16–21 (1977); Heider, J. G., et al., *Journal of Lipid Research*, Vol 24, pp. 1127–1134 (1983); U.S. Pat. No. 4,413,011 to Sircar, I. and Holmes, A., issued Nov. 1, 1983; U.S. Pat. No. 4,465,507 to Konno, K., et al., issued Aug. 14, 1984; Clark, S. B. and Tercyak, A. M., *Journal of Lipid Research*, Vol. 25, pp. 148–159 (1984); and U.S. Pat. No. 4,554,282 to Sircar, I. and Holmes, A., issued Nov. 19, 1985 describe various substituted amides, some of which are claimed to be used in treating atherosclerosis. However, the aforementioned compounds differ from the ones disclosed in the present invention in that the anilide fragment of the amide does not contain either an imino ether or a cyclic imino ether moiety.

SUMMARY OF THE INVENTION

Accordingly, the present invention relates to novel compounds having the formula I

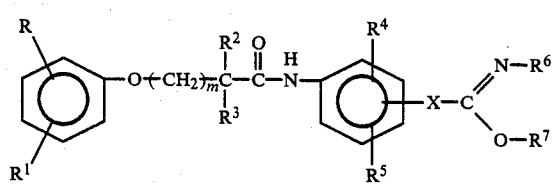

and their pharmaceutically acceptable acid addition salts where

R and $R^1$ are each independently hydrogen, straight or branched alkyl of from one to nine carbon atoms, cycloalkyl of from three to seven carbon atoms or alkoxy of from one to six carbons;

m is an integer from one to six;

$R^2$ and $R^3$ are each independently hydrogen, straight or branched alkyl of from one to nine carbon atoms, or when taken together with the carbon atom to which they are attached, form a cycloalkyl ring of from three to seven carbon atoms;

$R^4$ and $R^5$ are each independently hydrogen, straight or branched alkyl of from one to nine carbon atoms, cycloalkyl of from three to seven carbon atoms or alkoxy of from one to six carbons;

X is $-(CH_2)_n-$, $-O-CH_2-$ or

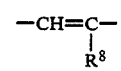

wherein n is zero to four and $R^8$ is hydrogen, straight or branched alkyl of from one to nine carbon atoms, or cycloalkyl of from three to seven carbon atoms;

$R^6$ is hydrogen;

$R^7$ is straight or branched alkyl of from one to nine carbon atoms, cycloalkyl of from three to seven carbon atoms, or $R^6$ and $R^7$ taken together are $-(CH_2)_p-$, $-CH=CH-$,

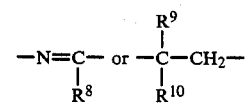

wherein p is two or three, $R^9$ and $R^{10}$ are each independently hydrogen, straight or branched alkyl of from one to nine carbon atoms, cycloalkyl of from three to seven carbon atoms, or $-CH_2OH$ and $R^8$ is as described above.

A more preferred group of compounds are those of formula II

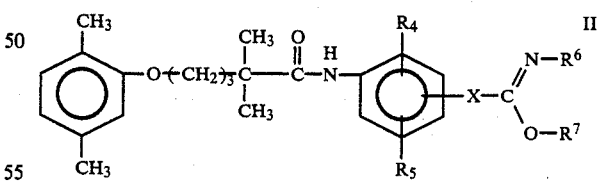

A most preferred group of compounds are those of formula II wherein $R^4$ and $R^5$ are each independently hydrogen, straight or branched alkyl of from one to six carbon atoms, or alkoxy of from one to six carbons;

X is $-(CH_2)_n-$, $-O-CH_2-$ or $-CH=CH-$ wherein n is zero to two;

$R^6$ is hydrogen;

$R^7$ is straight or branched alkyl of from one to six carbon atoms, cycloalkyl of from three to six carbons, or $R^6$ and $R^7$ taken together are $-(CH_2)_p-$, $-CH=CH-$, $$-N=C-, \text{ or } -\underset{R^{10}}{\overset{R^9}{\underset{|}{C}}}-CH_2-$$
$$\phantom{-N=}\underset{R^8}{|}$$

wherein p is two or three, $R^8$ is hydrogen, straight or branched alkyl of from one to six carbon atoms, or cycloalkyl of from three to six carbon atoms, $R^9$ and $R^{10}$ are each independently straight or branched alkyl of from one to six carbon atoms, cycloalkyl of from three to six carbon atoms, or —CH$_2$OH.

Additionally, the present invention is directed to a pharmaceutical composition useful for inhibiting the intestinal absorption of cholesterol in mammals comprising an acyl-coenzyme A: cholesterol acyltransferase-inhibitory effective amount of a compound of formula I

I and their pharmaceutically acceptable acid addition salts where

R and $R^1$ are each independently hydrogen, straight or branched alkyl of from one to nine carbon atoms, cycloalkyl of from three to seven carbon atoms or alkoxy of from one to six carbons;

m is an integer from one to six;

$R^2$ and $R^3$ are each independently hydrogen, straight or branched alkyl of from one to nine carbon atoms, or when taken together with the carbon atom to which they are attached, form a cycloalkyl ring of from three to seven carbon atoms;

$R^4$ and $R^5$ are each independently hydrogen, straight or branched alkyl of from one to nine carbon atoms, cycloalkyl of from three to seven carbon atoms or alkyloxy of from one to six carbons;

X is —(CH$_2$)$_n$—, —O—CH$_2$— or $$-CH=\underset{R^8}{\overset{|}{C}}-$$

wherein n is zero to four and $R^8$ is hydrogen, straight or branched alkyl of from one to nine carbon atoms, or cycloalkyl of from three to seven carbon atoms;

$R^6$ is hydrogen;

$R^7$ is straight or branched alkyl of from one to nine carbon atoms, cycloalkyl of from three to seven carbon atoms, or $R^6$ and $R^7$ taken together are —(CH$_2$)$_p$—, —CH=CH—, $$-N=\underset{R^8}{\overset{R^9}{\underset{|}{C}}}- \text{ or } -\underset{R^{10}}{\overset{|}{\underset{|}{C}}}-CH_2-$$

wherein p is two or three, $R^9$ and $R^{10}$ are each independently hydrogen, straight or branched alkyl of from one to nine carbon atoms, cycloalkyl of from three to seven carbon atoms, or —CH$_2$OH and $R^8$ is as described above with a pharmaceutically acceptable carrier.

Also, the present invention is directed to a novel method of inhibiting intestinal absorption of cholesterol in mammals comprising administering an acyl-coenzyme A: cholesterol acyltransferase-inhibitory effective amount of a compound of formula I as defined above in the description of the novel composition therefor.

Finally, the present invention is directed to methods for production of a compound of formula I as defined above in the description of the novel composition therefor.

DETAILED DESCRIPTION OF THE INVENTION

In the compounds of the formula I, the term alkyl of from one to nine carbon atoms is meant to include a straight alkyl group having the noted number of carbons, such as, for example, methyl, ethyl, propyl, butyl and the like or a branched alkyl group having the noted number of carbon atoms, such as, 2-propyl, 2-butyl and the like and isomers thereof.

The term cycloalkyl refers to a three to seven membered saturated hydrocarbon ring, such as, for example, cyclopropyl, cyclobutyl, cyclopentyl, cyclohexyl and the like.

The term alkoxy refers to an alkyl group, as defined above, attached to the parent molecular moiety through an oxygen atom.

The compounds of formula I are useful both in the free base form and in the form of acid addition salts. The two forms are within the scope of the present invention. Pharmaceutically acceptable acid addition salts are formed with inorganic and organic acids, such as, for example, hydrochloric, sulfuric, phosphoric, acetic, citric, gluconic, fumaric methanesulfonic and the like (see, for example, Berge, S. M., et al., "Pharmaceutical Salts", *Journal of Pharmaceutical Science*, 66, pp. 1–19 (1977)). The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated as well as solvated forms, including hydrated forms. In general, the solvated forms, including hydrated forms are equivalent to unsolvated forms and are intended to be encompassed within the scope of the present invention.

Certain of the compounds of the present invention may contain asymmetric carbon atoms or exist as geometric isomers. Thus, the invention includes the individual stereoisomers and or geometric isomers such as cis or trans, E (entgegen) or Z (zusammen), isomers and the mixtures thereof. The individual isomers may be prepared or isolated by methods known in the art.

Illustrative examples of compounds falling within the scope of the present invention are the following:

N-[3-(4,5-dihydro-4,4-dimethyl-2-oxazolyl)-2-methylphenyl]-5-(2,5-dimethylphenoxy)-2,2-dimethylpentanamide;

N-[3-(4,5-dihydro-4,4-dimethyl-2-oxazolyl)phenyl]-5-(2,5-dimethylphenoxy)-2,2-dimethylpentanamide;
N-[5-(4,5-dihydro-4,4-dimethyl-2oxazolyl)-2-methylphenyl]-5-(2,5-dimethylphenoxy)-2,2-dimethylpentanamide;
N-[3-(4,5-dihydro-2-oxazolyl)-2-methylphenyl]-5-(2,5-dimethylphenoxy)-2,2-dimethylpentanamide;
N-[3-[(4,5-dihydro-4,4-dimethyl-2-oxazolyl)methyl]-4-methylphenyl]-5-(2,5-dimethylphenoxy)-2,2-dimethylpentanamide;
N-[3-[2-(4,5-dihydro-4,4-dimethyl-2-oxazolyl)ethyl]-4-methoxyphenyl]-5-(2,5-dimethylphenoxy)-2,2-dimethylpentanamide;
N-[3-[2(4,5-dihydro-4,4-dimethyl-2-oxazolyl)ethenyl]phenyl]-5-(2,5-dimethylphenoxy)-2,2-dimethylpentanamide;
(E)-N-[5-[2-(4,5-dihydro-4,4-dimethyl-2-oxazolyl)ethenyl]-2-methoxyphenyl]-5-(2,5-dimethylphenoxy)-2,2-dimethylpentanamide;
N-[5-[(4,5-dihydro-4,4-dimethyl-2-oxazolyl)methyl]-2-methoxyphenyl]-5-(2,5-dimethylphenoxy)-2,2-dimethylpentanamide;
N-[3-[(4,5-dihydro-4,4-dimethyl-2-oxazolyl)methoxy]phenyl]-5-(2,5-dimethylphenoxy)-2,2-dimethylpentanamide;
N-[5-[(4,5-dihydro-4,4-dimethyl-2-oxazolyl)methyl]-2-methylphenyl]-5-(2,5-dimethylphenoxy)-2,2-dimethylpentanamide;
N-[3-(5,6-dihydro-4H-1,3-oxazin-2-yl)phenyl]-5-(2,5-dimethylphenoxy)-2,2-dimethylpentanamide;
N-[3-[4,5-dihydro-4,4-bis(hydroxymethyl)-2-oxazolyl]phenyl]-5-(2,5-dimethylphenoxy)-2,2-dimethylpentanamide;
N-[5-(4,5-dihydro-4,4-dimethyl-2-oxazolyl)-2-methoxyphenyl]-5-(2,5-dimethylphenoxy)-2,2-dimethylpentanamide;
N-[5-[4,5-dihydro-4,4-bis(hydroxymethyl)-2-oxazolyl]-2-methoxyphenyl]-5-(2,5-dimethylphenoxy)-2,2-dimethylpentanamide;
N-[3-(4,5-dihydro-4,4-dimethyl-2-oxazolyl)-4-methoxyphenyl]-5-(2,5-dimethylphenoxy)-2,2-dimethylpentanamide;
N-[5-(4,5-dihydro-4,4-dimethyl-2-oxazolyl)-2,4-dimethoxyphenyl]-5-(2,5-dimethylphenoxy)-2,2-dimethylpentanamide;
N-[5-(5,6-dihydro-4H-1,3-oxazin-2-yl)-2-methoxyphenyl]-5-(2,5-dimethylphenoxy)-2,2-dimethylpentanamide;
5-(2,5-dimethylphenoxy)-N-[3-(iminomethoxymethyl)phenyl]-2,2-dimethylpentanamide monohydrochloride;
5-(2,5-dimethylphenoxy)-2,2-dimethyl-N-[3-(2-oxazolyl)phenyl]-pentanamide; and
5-(2,5-dimethylphenoxy)-2,2-dimethyl-N-[3-(5-methyl-1,3,4-oxadiazol-2-yl)phenyl]pentanamide.

The process of preparing compounds of the present invention is described generally, as follows:

A compound having the formula I

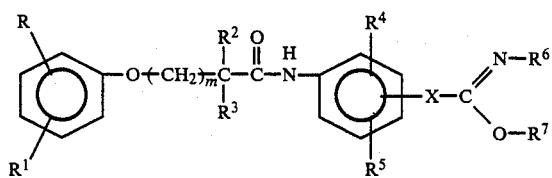

where
R and $R^1$ are each independently hydrogen, straight or branched alkyl of from one to nine carbon atoms, cycloalkyl of from three to seven carbon atoms or alkoxy of from one to six carbons;
m is an integer from one to six;
$R^2$ and $R^3$ are each independently hydrogen, straight or branched alkyl of from one to nine carbon atoms, or when taken together with the carbon atom to which they are attached, form a cycloalkyl ring of from three to seven carbon atoms;
$R^4$ and $R^5$ are each independently hydrogen, straight or branched alkyl of from one to nine carbon atoms, cycloalkyl of from three to seven carbon atoms or alkoxy of from one to six carbons;
X is $-(CH_2)_n-$, $-O-CH_2-$ or

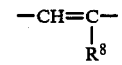

wherein n is zero to four and $R^8$ is hydrogen, straight or branched alkyl of from one to nine carbon atoms, or cycloalkyl of from three to seven carbon atoms;
$R^6$ is hydrogen;
$R^7$ is straight or branched alkyl of from one to nine carbon atoms, cycloalkyl of from three to seven carbon atoms, or $R^6$ and $R^7$ taken together are $-(CH_2)_p-$, $-CH=CH-$,

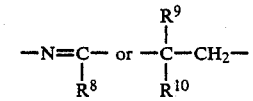

wherein p is two or three, $R^9$ and $R^{10}$ are each independently hydrogen, straight or branched alkyl of from one to nine carbon atoms, cycloalkyl of from three to seven carbon atoms, or $-CH_2OH$ and $R^8$ is as described above; is prepared by coupling a compound of formula III

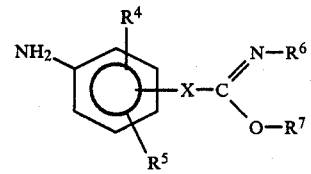

wherein $R^4$, $R^5$, X, $R^6$ and $R^7$ are as described above with a compund of formula IV

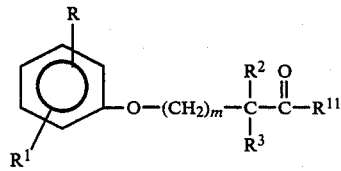

wherein $R^{11}$ is a leaving group, R, $R^1$, m, $R^2$ and $R^3$ are as described above.
Preferred coupling methods involve contacting a compound of formula III with acylhalides of the formula V

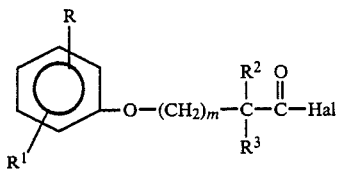

V wherein Hal is halo, preferably chloro or bromo, and R, R¹, m, R² and R³ are as described above.

The reaction is carried out in nonaqueous solvent such as acetonitrile, tetrahydrofuran or methylene chloride, preferably methylene chloride, with an added organic base such as triethylamine or pyridine, preferably triethylamine, if needed at temperatures between −10° C. and the reflux temperature of the solvent, preferably at 0° C.

Compounds of the formula III are either known or capable of being prepared by methods known in the art.

Compounds of formula IV are obtained by appropriately activating a compound of formula VI

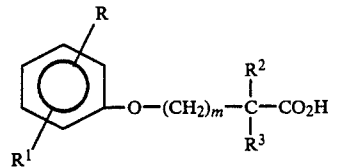

VI wherein R, R¹, m, R² and R³ are as described above with a carboxyl activating group such as described in E. Schroder and K. Lübke, "The Peptides", Vol. 1, Chapt. III, Academic Press, 1965.

Compounds of formula VI are either known or capable of being prepared by methods known in the art.

A compound of formula I also may be prepared by contacting a compound of formula VII

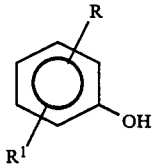

VII wherein R and R¹ are as described above with a compound of formula VIII

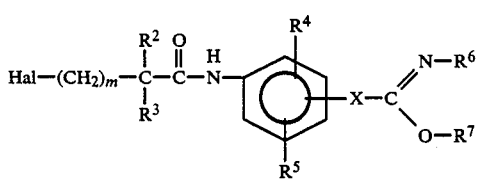

VIII wherein Hal, m, R², R³, R⁴, R⁵, X, R⁶ and R⁷ are as described above.

The reaction is carried out in the presence of a base such as, for example, sodium hydroxide, potassium carbonate and the like in nonaqueous solvent such as, for example, tetrahydrofuran at temperatures between 0° C. and the reflux temperature of the solvent, preferably at the reflux temperature of the solvent.

Compounds of formula VII are either known or capable of being prepared by methods known in the art.

Compounds of formula VIII are obtained by contacting a compound of formula IX

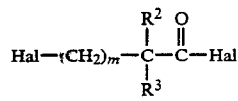

IX wherein Hal, m, R² and R³ are as described above with a compound of formula III.

The reaction is carried out in nonaqueous solvent such as acetonitrile, tetrahydrofuran or methylene chloride, preferably methylene chloride, with an added organic base such as triethylamine or pyridine, preferably triethylamine, if needed at temperatures between −10° C. and the reflux temperature of the solvent, preferably at 0° C.

Compounds of formula IX are either known or capable of being prepared by methods known in the art.

The products of the reactions described herein are isolated by conventional means such as chromatography, recrystallization, distillation, and the like. Generally, the starting materials are known, commercially available or synthesized by known methods.

The compounds of the present invention were tested for their ability to inhibit the esterification of cholesterol by the enzyme acyl-CoA: cholesterol acyltransferase (ACAT). The data in the table below is expressed as $IC_{50}$ values, i.e. the concentration of test compound required to inhibit cholesteryl oleate formation to 50% of control. The data in the table shows the ability of representative compounds of the present invention to potently inhibit ACAT.

TABLE

| | BIOLOGICAL ACTIVITY OF COMPOUNDS OF FORMULA I | |
|---|---|---|
| Example Number | Compound | $IC_{50}$ (μ Moles) |
| 1 | N—[3-(4,5-dihydro-4,4-dimethyl-2-oxazolyl)-2-methylphenyl]-5-(2,5-dimethylphenoxy)-2,2-dimethylpentanamide | 24 |
| 1a | N—[3-(4,5-dihydro-4,4-dimethyl-2-oxazolyl)phenyl]-5-(2,5-dimethylphenoxy)-2,2-dimethylpentanamide | 22 |
| 1b | N—[5-(4,5-dihydro-4,4-dimethyl-2-oxazolyl)-2-methylphenyl]-5-(2,5-dimethylphenoxy)-2,2-dimethylpentanamide | 5.5 |
| 1c | N—[3-(4,5-dihydro-2-oxazolyl)-2-methylphenyl]-5-(2,5-dimethylphenoxy)-2,2-dimethylpentanamide | 10 |
| 1d | N—[3-[(4,5-dihydro-4,4-dimethyl-2-oxazolyl)methyl]-4-methylphenyl]-5-(2,5-dimethylphenoxy)-2,2-dimethylpentanamide | 1 |
| 2 | N—[3-[2-(4,5-dihydro-4,4-dimethyl-2-oxazolyl)ethyl]-4-methoxyphenyl]-5-(2,5-dimethylphenoxy)-2,2-dimethylpentanamide | 3.7 |
| 2a | N—[3-[2-(4,5-dihydro-4,4-dimethyl-2-oxazolyl)ethenyl]phenyl]-5-(2,5-dimethylphenoxy)-2,2-dimethylpentanamide | 9.4 |
| 2b | (E)-N—[5-[2-(4,5-dihydro-4,4-dimethyl-2-oxazolyl)ethenyl]-2-methoxyphenyl]-5-(2,5-dimethylphenoxy)-2,2-dimethylpentanamide | 8 |
| 3 | N—[5-[(4,5-dihydro-4,4-dimethyl-2-oxazolyl)methyl]-2-methoxyphenyl]-5-(2,5-dimethylphenoxy)-2,2- | 5.5 |

TABLE-continued
BIOLOGICAL ACTIVITY OF COMPOUNDS
OF FORMULA I

| Example Number | Compound | $IC_{50}$ ($\mu$ Moles) |
|---|---|---|
| 3a | N—[3-[(4,5-dihydro-4,4-dimethyl-2-oxazolyl)methoxy]phenyl]-5-(2,5-dimethylphenoxy)-2,2-dimethylpentanamide | 9.2 |
| 3b | N—[5-[(4,5-dihydro-4,4-dimethyl-2-oxazolyl)methyl]-2-methylphenyl]-5-(2,5-dimethylphenoxy)-2,2-dimethylpentanamide | 0.8 |
| 4 | N—[3-(5,6-dihydro-4H-1,3-oxazin-2-yl)phenyl]-5-(2,5-dimethylphenoxy)-2,2-dimethylpentanamide | 20 |
| 4b | N—[5-(4,5-dihydro-4,4-dimethyl-2-oxazolyl)-2-methoxyphenyl]-5-(2,5-dimethylphenoxy)-2,2-dimethylpentanamide | 9 |
| 4d | N—[3-(4,5-dihydro-4,4-dimethyl-2-oxazolyl)-4-methoxyphenyl]-5-(2,5-dimethylphenoxy)-2,2-dimethylpentanamide | 19 |
| 4e | N—[5-(4,5-dihydro-4,4-dimethyl-2-oxazolyl)-2,4-dimethoxyphenyl]-5-(2,5-dimethylphenoxy)-2,2-dimethylpentanamide | 9 |
| 4f | N—[5-(5,6-dihydro-4H-1,3-oxazin-2-yl)-2-methoxyhenyl]-5-(2,5-dimethylphenoxy)-2,2-dimethylpentanamide | 18 |
| 4g | 5-(2,5-dimethylphenoxy)-N—[3-(iminomethoxymethyl)phenyl]-2,2-dimethylpentanamide monohydrochloride | 13 |
| 4h | 5-(2,5-dimethylphenoxy)-2,2-dimethyl-N—[3-(2-oxazolyl)phenyl]-pentanamide | 23 |
| 5 | 5-(2,5-dimethylphenoxy)-2,2-dimethyl-N—[3-(5-methyl-1,3,4-oxadiazol-2-yl)phenylpentanamide | 21 |

The in vitro test employed is more fully described in Field, F. J. and Salome, R. G., *Biochemica et Biophysica Acta*, 712, pp. 557–570 (1982). The assay evaluates the ability of a test compound to inhibit the esterification of cholesterol using endogenous cholesterol of a rabbit intestinal microsomal fraction and exogenous $^{14}C$-oleoyl-CoA as reactants.

Therefore, the compounds of the present invention are useful in pharmaceutical formulations for preventing absorption of dietary cholesterol or the reabsorption of cholesterol which has been released into the intestines through endogenous regulatory mechanisms.

The present invention also includes a method for treating hypercholesterolemia comprising administering to mammals, including humans, the corresponding pharmaceutical composition. The composition contains a compound of formula I as defined before in an appropriate unit dosage form.

For preparing pharmaceutical compositions from the compounds of the present invention, pharmaceutically acceptable carriers can be either solid or liquid. Solid form preparations include powders, tablets, pills, capsules, and dispersible granules. A solid carrier can be one or more substances which may also act as diluents, flavoring agents, solubilizers, lubricants, suspending agents, binders, preservatives, tablet disintegrating agents or an encapsulating material.

In powders, the carrier is a finely divided solid which is in a mixture with the finely divided active component.

In tablets, the active compound is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets and lozenges can be used as solid dosage forms suitable for oral administration.

Liquid form preparations include solutions, suspensions and emulsions, for example, water or water propylene glycol solutions.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solution,s suspensions and emulsions. These preparations may contain, in addition to the active component, colorants, flavors, stabilizers, buffers, artificial and natural sweetners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules and powders in vials or ampules. Also, the unit dosage form can be a capsule, tablet, cachet or lozenge itself or it can be the appropriate number of any of these in packaged form.

The quantity of active component in a unit dose preparation may be varied or adjusted from 50 mg to 500 mg preferably 100 mg to 300 mg according to the particular application and the potency of the active component. The composition can, if desired, also contain other compatible therapeutic agents.

The dosage range for a 70 kg mammal is from 1 mg/kg to 100 mg/kg of body weight per day or preferably 3 mg/kg to 15 mg/kg of body weight per day when the compounds of the present invention are used therapeutically to inhibit the intestinal absorption of cholesterol. However, dosages may be varied depending upon the compound used, the severity of the condition being treated and the requirements of the patient. Determination of the appropriate dosage for a particular situation is within the skill of the art.

The invention is further illustrated but not limited by the following examples.

EXAMPLE 1

N-[3-(4,5-Dihydro-4,4-dimethyl-2-oxazolyl)-2-methylphenyl]-5-(2,5-dimethylphenoxy)-2,2-dimethylpentanamide A solution of 2-methyl-3-nitrobenzoyl chloride, 0.2 mol, (U.S. Pat. No. 4,065,477) in dichloromethane is added to 0.4 mol of 2-amino-2-methyl-1-propanol (Aldrich Chemical Company) with ice cooling. The mixture is allowed to stand overnight, water added and the solid filtered to give 20.8 g. The organic layer is washed with water, separated and evaporated to give 28.1 g. The two crops of material are combined and dissolved in 2-propanol. The 2-propanol solution is concentrated to give 40.2 g of N-(2-hydroxy-1,1-dimethylethyl)-2-methyl-3-nitrobenzamide; mp 144°–145° C.

Thionyl chloride, 37 ml, is added dropwise with stirring to 39.7 g (0.1575 mol) of N-(2-hydroxy-1,1-dimethylethyl)-2-methyl-3-nitrobenzamide. The mixture is allowed to stand overnight, poured into diethylether, filtered and the solvent evaporated to give 33.4 g of 4,5-dihydro-4,4-dimethyl-2-(2-methyl-3-nitrophenyl)oxazole as a pale yellow oil which crystallizes on cooling; mp 60°–61° C.

To 29.82 g of 4,5-dihydro-4,4-dimethyl-2-(2-methyl-3-nitrophenyl)oxazole in 500 ml of tetrahydrofuran is added 0.5 g of 10% palladium on barium sulfate. The mixture is exposed to hydrogen gas until the appropriate quantity of hydrogen is taken up, filtered and the solvent evaporated to give 24.7 g of 3-(4,5-dihydro-4,4-dimethyl-2-oxazolyl)-2-methylbenzenamine as a gum which crystallizes on cooling; mp 45° C.

To a solution of 10.2 g (0.05 mol) of 3-(4,5-dihydro-4,4-dimethyl-2-oxazolyl)-2-methylbenzenamine and 10 ml of triethylamine in dichloromethane is added 13.4 g (0.05 mol) of 5-(2,5-dimethylphenoxy)-2,2-dimethylpentanoyl chloride (U.S. Pat. No. 4,285,951). The mixture is worked up, chromatographed over silica gel and eluted with toluene-diethyl ether (2:1) to give 13 g of N-[3-(4,5-dihydro-4,4-dimethyl-2-oxazolyl)-2-methylphenyl]-5-(2,5-dimethylphenoxy)-2,2-dimethylpentanamide; mp 51°–52° C.

In a process analogous to Example 1 using appropriate starting materials the corresponding compounds of formula I are prepared as follows:

EXAMPLE 1a

N-[3-(4,5-Dihydro-4,4-dimethyl-2-oxazolyl)phenyl]-5-(2,5-dimethylphenoxy)-2,2-dimethylpentanamide mp 92°–94° C.

EXAMPLE 1b

N-[5-(4,5-Dihydro-4,4-dimethyl-2-oxazolyl)-2-methylphenyl]-5-(2,5-dimethylphenoxy)-2,2-dimethylpentanamide mp 79°–80° C.

EXAMPLE 1c

N-[3-(4,5-Dihydro-2-oxazolyl)-2-methylphenyl]-5-(2,5-dimethylphenoxy)-2,2-dimethylpentanamide mp 98°–100° C.

EXAMPLE 1d

N-[3-[(4,5-Dihydro-4,4-dimethyl-2-oxazolyl)methyl]-4-methylphenyl]-5-(2,5-dimethylphenoxy)-2,2-dimethylpentanamide mp 92°–93° C.

EXAMPLE 2

N-[3-[2-(4,5-Dihydro-4,4-dimethyl-2-oxazolyl)ethyl]-4-methoxyphenyl]-5-(2,5-dimethylphenoxy)-2,2-dimethylpentanamide A mixture of 2-methoxy-5-nitrobenzaldehyde, 16 g, (U.S. Pat. No. 4,367,234), 2,4,4-trimethyl-2-oxazoline, 30 ml, (Aldrich Chemical Company), para toluenesulfornic acid, 0.5 g, in toluene, 100 ml, is refluxed overnight under a water separator. The mixture is evaporated, the residue dissolved in diethylether, 800 ml, and washed with water. The diethyl ether layer is separated, concentrated, and filtered to give 11.1 g of 4,5-dihydro-2-[2-(2-methoxy-5-nitrophenyl)ethenyl]-4,4-dimethyloxazole after recrystallization from diisopropyl ether; mp 115°–116° C.

Raney nickel, 3 g, is added to a solution of 4,5-dihydro-2-[2-(2-methoxy-5-nitrophenyl)ethenyl]-4,4-dimethyloxazole, 10.9 g, in methanol, 500 ml. The mixture is exposed to hydrogen gas until the appropriate quantity of hydrogen is taken up, filtered and the solvent evaporated to give 10.2 g of 3-[2-(4,5-dihydro-4,4-dimethyl-2-oxazolyl)ethyl]-4-methoxybenzenamine as a gum. To an ice cold solution of the previous crude gum and 7 ml of triethylamine in chloroform is added 10.5 g of 5-(2,5-dimethylphenoxy)-2,2-dimethylpentanoyl chloride (U.S. Pat. No. 4,285,951). The mixture is worked up, chromatographed over silica gel and eluted with diethylether to give 10.5 g of N-[3-[2-(4,5-dihydro-4,4-dimethyl-2-oxazolyl)ethyl]-4-methoxyphenyl]-5-(2,5-dimethylphenoxy)-2,2-dimethylpentanamide as a gum; thin layer chromatography on silica gel: $R_f = 0.57$ (ethyl acetate).

In a process analogous to Example 2 using appropriate starting materials the corresponding compounds of formula I are prepared as follows:

EXAMPLE 2a

N-[3-[2-(4,5-Dihydro-4,4-dimethyl-2-oxazolyl)ethenyl]phenyl]-5-(2,5-dimethylphenoxy)-2,2-dimethylpentanamide gum; thin layer chromatography on silica gel: $R_f = 0.47$ (chloroform:ethyl acetate 3:1).

EXAMPLE 2b (E)-N-[5-[2-(4,5-Dihydro-4,4-dimethyl-2-oxazolyl)ethenyl]-2-methoxyphenyl]-5-(2,5-dimethylphenoxy)-2,2-dimethylpentanamide viscous liquid; thin layer chromatography on silica gel: $R_f = 0.67$ (ethyl acetate).

EXAMPLE 3

N-[5-[(4,5-Dihydro-4,4-dimethyl-2-oxazolyl)methyl]-2-methoxyphenyl]-5-(2,5-dimethylphenoxy)-2,2-dimethylpentanamide A mixture of 2-amino-2-methyl-1-propanol, 7.2 g (0.05 mol), (Aldrich Chemical Company) and 4-methoxy-3-nitrobenzeneacetic acid, 16.7 g (0.079 mol), (*Journal of the American Chemical Society*, Vol. 70, pp. 2837–2843, (1948)) is refluxed overnight in xylene, 100 ml, under a water separator. The mixture is diluted with toluene, filtered, washed with an aqueous solution of potassium bicarbonate and water. The organic layer is separated and evaporated. The resulting gum is chromatographed over silica gel and eluted with ethyl acetate to give 7.6 g of 4,5-dihydro-2-[(4-methoxy-3-nitrophenyl)methyl]-4,4-dimethyloxazole after recrystallization from hexane; mp 88°–90° C.

Raney nickel, 0.5 g, is added to a solution of 4,5-dihydro-2-[(4-methoxy-3-nitrophenyl)methyl]-4,4-dimethyloxazole, 7.52 g, in methyl alcohol, 100 ml. The mixture is exposed to hydrogen gas until the appropriate quantity of hydrogen is taken up, filtered and the solvent evaporated to give 5.85 g of 5-(4,5-dihydro-4,4-dimethyl-2-oxazolyl)-2-methoxybenzenamine after recrystallization from diisopropyl ether; mp 108°–110° C.

To an ice cold solution of 5-(4,5-dihydro-4,4-dimethyl-2-oxazolyl)-2-methoxybenzenamine, 5.75 g, and 4 ml of triethylamine in dichloromethane, 100 ml, is added 6.6 g of 5-(2,5-dimethylphenoxy)-2,2-dimethylpentanoyl chloride (U.S. Pat. No. 4,285,951). The mixture is worked up to give 6.4 g of N-[5-[(4,5-dihydro-4,4-dimethyl-2-oxazolyl)methyl]-2-methoxyphenyl]-5-(2,5-dimethylphenoxy) 2,2-dimethylpentanamide after recrystallization from hexane; mp 79°–80° C.

The process analogous to Example 3 using appropriate starting materials the corresponding compounds of formula I are prepared as follows:

EXAMPLE 3a

N-[3-[(4,5-Dihydro-4,4-dimethyl-2-oxazolyl)methoxy]phenyl]-5-(2,5-dimethylphenoxy)-2,2-dimethylpentanamide bp about 200° C. at 0.1 mm.

EXAMPLE 3b

N-[5-[(4,5-Dihydro-4,4-dimethyl-2-oxazolyl)methyl]-2-methylphenyl]-5-(2,5-dimethylphenoxy)-2,2-dimethylpentanamide mp 88°–89° C.

EXAMPLE 4

N-[3-(5,6-Dihydro-4H-1,3-oxazin-2-yl)phenyl]-5-(2,5-dimethylphenoxy)-2,2-dimethylpentanamide To an ice cold solution of 3-(5,6-dihydro-4H-1,3-oxazin-2-yl)benzenamine, 8.8 g (0.05 mol), (Journal of the American Chemical Society, Vol. 59, pp. 2259–2261, (1937)) and triethylamine, 10 ml, in dichloromethane, 300 ml, is added 5-(2,5-dimethylphenoxy)-2,2-dimethylpentanoyl chloride, 13.4 g (0.05 mol), (U.S. Pat. No. 4,285,951). The mixture is worked up to give 18.8 g of N-[3-(5,6-dihydro-4H-1,3-oxazin-2-yl)phenyl]-5-(2,5-dimethylphenoxy)-2,2-dimethylpentanamide after recrystallization from diisopropyl ether; mp 114°–115° C.

In a process analogous to Example 4 using appropriate starting materials the corresponding compounds of formula I are prepared as follows:

EXAMPLE 4a

N-[3-[4,5-Dihydro-4,4-bis(hydroxymethyl)-2-oxazolyl]phenyl]-5-(2,5-dimethylphenoxy)-2,2-dimethylpentanamide mp 117°–119° C.

EXAMPLE 4b

N-[5-(4,5-Dihydro-4,4-dimethyl-2-oxazolyl)-2-methoxyphenyl]-5-(2,5-dimethylphenoxy)-2,2-dimethylpentanamide mp 73°–75° C.

EXAMPLE 4c

N-[5-[4,5-Dihydro-4,4-bis(hydroxymethyl)-2-oxazolyl]-2-methoxyphenyl]-5-(2,5-dimethylphenoxy)-2,2-dimethylpentanamide mp 81°–84° C.

EXAMPLE 4d

N-[3-(4,5-Dihydro-4,4-dimethyl-2-oxazolyl)-4-methoxyphenyl]-5-(2,5-dimethylphenoxy)-2,2-dimethylpentanamide mp 137°–138° C.

EXAMPLE 4e

N-[5-(4,5-Dihydro-4,4-dimethyl-2-oxazolyl)-2,4-dimethoxyphenyl]-5-(2,5-dimethylphenoxy)-2,2-dimethylpentanamide mp 94°–95° C.

EXAMPLE 4f

N-[5-(5,6-Dihydro-4H-1,3-oxazin-2-yl)-2-methoxyphenyl]-5-(2,5-dimethylphenoxy)-2,2-dimethylpentanamide mp 111°–112° C.

EXAMPLE 4g 5-(2,5-Dimethylphenoxy)-N-[3-(iminomethoxymethyl)phenyl]-2,2-dimethylpentanamide monohydrochloride In an acylation process analogous to Example 4 by substituting 3-aminobenzonitrile (Aldrich Chemical Company) for 3-(5,6-dihydro-4H-1,3-oxazin-2-yl)benzenamine one obtains N-(3-cyanophenyl)-5-(2,5-dimethylphenoxy)-2,2-dimethylpentanamide. The nitrile is then converted using methyl alcohol and hydrochloric acid to 5-(2,5-dimethylphenoxy)-N-[3-(iminomethoxymethyl)phenyl]-2,2-dimethylpentanamide monohydrochloride; mp 118°–120° C. (dec.).

EXAMPLE 4h 5-(2,5-Dimethylphenoxy)-2,2-dimethyl-N-[3-(2-oxazolyl)phenyl]-pentanamide In a process analogous to Example 4 by substituting 3-(2-oxazolyl)benzenamine (Journal of Organic Chemistry, Vol. 42, pp. 3208–3209, (1977)) for 3-(5,6-dihydro-4H-1,3-oxazin-2-yl)benzenamine one obtains 5-(2,5-dimethylphenoxy)-2,2-dimethyl-N-[3-(2-oxazolyl)phenyl]-pentanamide; mp 67°–69° C.

EXAMPLE 5

5-(2,5-Dimethylphenoxy)-2,2-dimethyl-N-[3-(5-methyl1,3,4-oxadiazol-2-yl)phenyl]pentanamide 3-Nitrobenzoic acid, hydrazide, 24.5 g, (Chemical Abstracts, Vol. 102, 148507r (1983)) and 1,1,1-triethoxyethane are refluxed overnight. The mixture is cooled, filtered, and washed with hexane to give 21.9 g of 2-methyl-5-(3-nitrophenyl)-1,3,4-oxadiazole after recrystallization from 2-propanol; mp 154°–156° C.

Iron powder, 27.9 g (0.5 mol), is added to a mixture of 2-methyl-5-(3-nitrophenyl)-1,3,4-oxadiazole, (0.053 mol), in 1000 ml of ethyl alcohol with stirring. The mixture is heated to reflux and 1.73 ml of concentrated hydrochloric acid in 10 ml of ethyl alcohol is added dropwise. The mixture is reluxed three hours, 20 ml of 1 normal potassium hydroxide is added, the mixture filtered, and the filtrate evaporated. The residue is dissolved in dichloromethane, washed with water, and the methylene chloride layer separated and evaporated to give 7.05 g of 3-(5-methyl-1,3,4-oxadiazol-2-yl) benzenamine after recrystallization from 2-propanol; mp 139°-140° C.

To a solution of 7.05 g (0.04 mol) of 3-(5-methyl-1,3,4-oxadiazol-2-yl)benzenamine and 10 ml of triethylamine in 300 ml of dichloromethane is added 11 g of 5-(2,5-dimethylphenoxy)-2,2-dimethylpentanoyl chloride (U.S. Pat. No. 4,285,951). The mixture is worked up, the crude product slurried in ethyl acetate and filtered through silica gel. The solvent is evaporated to give 1.2 g of 5-(2,5-dimethylphenoxy)-2,2-dimethyl-N-[3-(5-methyl-1,3,4-oxadiazol-2-yl)phenyl]pentanamide after recrystallization from 2-propanol; mp 90°-92° C.

We claim:

1. A compound having the formula

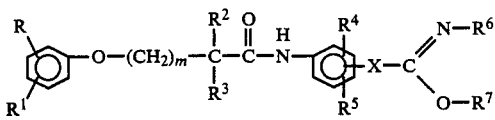

or a pharmaceutically acceptable acid addition salt thereof where

R and $R^1$ are each independently hydrogen, straight or branched alkyl of from one to nine carbon atoms, cycloalkyl of from three to seven carbon atoms or alkoxy of from one to six carbons;

m is an integer from one to six;

$R^2$ and $R^3$ are each independently hydrogen, straight or branched alkyl of from one to nine carbon atoms, or when taken together with the carbon atom to which they are attached, form a cycloalkyl ring of from three to seven carbon atoms;

$R^4$ and $R^5$ are each independently hydrogen, straight or branched alkyl of from one to nine carbon atoms, cycloalkyl of from three to seven carbon atoms or alkoxy of from one to six carbons;

X is —$(CH_2)_n$—, —O—$CH_2$— or

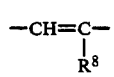

wherein n is zero to four and $R^8$ is hydrogen, straight or branched alkyl of from one to nine carbon atoms, or cycloalkyl of from three to seven carbon atoms;

$R^6$ and $R^7$ taken together are —$(CH_2)_p$—, —CH=CH—,

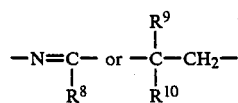

wherein p is two or three, $R^9$ and $R^{10}$ are each independently hydrogen, straight or branched alkyl of from one to nine carbon atoms, cycloalkyl of from three to seven carbon atoms, or —$CH_2OH$ and $R^8$ is as described above.

2. A compound as defined in claim 1 having the formula

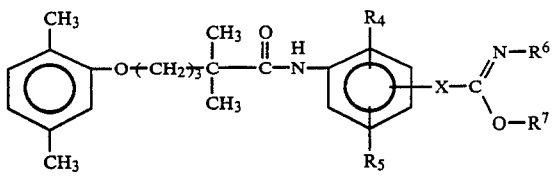

3. A compound as defined in claim 2 wherein $R^4$ and $R^5$ are each independently hydrogen, straight or branched alkyl of from one to six carbon atoms, or alkoxy of from one to six carbons;

X is —$(CH_2)_n$—, —O—$CH_2$— or —CH=CH— wherein n is zero to two;

$R^6$ and $R^7$ taken together are —$(CH_2)_p$—, —CH=CH—,

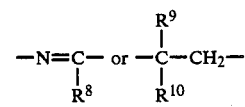

wherein p is two or three, $R^8$ is hydrogen, straight or branched alkyl of from one to six carbon atoms, or cycloalkyl of from three to six carbon atoms, $R^9$ and $R^{10}$ are each independently straight or branched alkyl of from one to six carbon atoms, cycloalkyl of from three to six carbons, or —$CH_2OH$.

4. A compound as defined in claim 3 having the name N-[3-(4,5-dihydro-4,4-dimethyl-2-oxazolyl)-2-methylphenyl]-5-(2,5-dimethylphenoxy)-2,2-dimethylpentanamide.

5. A compound as defined in claim 3 having the name N-[3-(4,5-dihydro-4,4-dimethyl-2-oxazolyl)phenyl]-5-(2,5-dimethylphenoyx)-2,2-dimethylpentanamide.

6. A compound as defined in claim 3 having the name N-[5-(4,5-dihydro-4,4-dimethyl-2-oxazolyl)-2-methylphenyl]-5-(2,5-dimethylphenoxy)-2,2-dimethylpentanamide.

7. A compound as defined in claim 3 having the name N-[3-(4,5-dihydro-2-oxazolyl)-2-methylphenyl]-5-(2,5-dimethylphenoxy)-2,2-dimethylpentanamide.

8. A compound as defined in claim 3 having the name N-[3-[(4,5-dihydro-4,4-dimethyl-2-oxazolyl)methyl]-4-methylphenyl]-5-(2,5-dimethylphenoxy)-2,2-dimethylpentanamide.

9. A compound as defined in claim 3 having the name N-[3-[2-(4,5-dihydro-4,4-dimethyl-2-oxazolyl)ethyl]-4-methoxyphenyl]-5-(2,5-dimethylphenoxy)-2,2-dimethylpentanamide.

10. A compound as defined in claim 3 having the name N-[3-[2-(4,5-dihydro-4,4-dimethyl-2-oxazolyl)ethenyl]phenyl]-5-(2,5-dimethylphenoxy)-2,2-dimethylpentanamide.

11. A compound as defined in claim 3 having the name (E)-N-[5-[2-(4,5-dihydro-4,4-dimethyl-2-oxazolyl)ethenyl]-2-methoxyphenyl]-5-(2,5-dimethylphenoxy)-2,2-dimethylpentanamide.

12. A compound as defined in claim 3 having the name N-[5-[(4,5-dihydro-4,4-dimethyl-2-oxazolyl)me- 13. A compound as defined in claim 3 having the name N-[3-[(4,5-dihydro-4,4-dimethyl-2-oxazolyl)methoxy]phenyl]-5-(2,5-dimethylphenoxy)-2,2-dimethylpentanamide.

14. A compound as defined in claim 3 having the name N-[5-[4,5-dihydro-4,4-dimethyl-2-oxazolyl)methyl]-2-methylphenyl]-5-(2,5-dimethylphenoxy)-2,2-dimethylpentanamide.

15. A compound as defined in claim 3 having the name N-[3-(5,6-dihydro-4H-1,3-oxazin-2-yl)phenyl]-5-(2,5-dimethylphenoxy)-2,2-dimethylpentanamide.

16. A compound as defined in claim 3 having the name N-[3-[4,5-dihydro-4,4-bis(hydroxymethyl)-2-oxazolyl]phenyl]-5-(2,5-dimethylphenoxy)-2,2-dimethylpentanamide.

17. A compound as defined in claim 3 having the name N-[5-(4,5-dihydro-4,4-dimethyl-2-oxazolyl)-2-methoxyphenyl]-5-(2,5-dimethylphenoxy)-2,2-dimethylpentanamide.

18. A compound as defined in claim 3 having the name N-[5-[4,5-dihydro-4,4-bis(hydroxymethyl)-2-oxazolyl]-2-methoxyphenyl]-5-(2,5-dimethylphenoxy)-2,2-dimethylpentanamide.

19. A compound as defined in claim 3 having the name N-[3-(4,5-dihydro-4,4-dimethyl-2-oxazolyl)-4-methoxyphenyl]-5-(2,5-dimethylphenoxy)-2,2-dimethylpentanamide.

20. A compound as defined in claim 3 having the name N-[5-(4,5-dihydro-4,4-dimethyl-2-oxazolyl)-2,4-dimethoxyphenyl]-5-(2,5-dimethylphenoxy)-2,2-dimethylpentanamide.

21. A compound as defined in claim 3 having the name N-[5-(5,6-dihydro-4H-1,3-oxazin-2-yl)-2-methoxyphenyl]-5-(2,5-dimethylphenoxy)-2,2-dimethylpentanamide.

22. A compound as defined in claim 3 having the name 5-(2,5-dimethylphenoxy)-2,2-dimethyl-N-[3-(2-oxazolyl)phenyl]-pentanamide.

23. A compound as defined in claim 3 having the name 5-(2,5-dimethylphenoxy)-2,2-dimethyl-N-[3-(5-methyl-1,3,4-oxadiazol-2-yl)phenyl]pentanamide.

24. A pharmaceutical composition useful for inhibiting the intestinal absorption of cholesterol in mammals comprising an acylcoenzyme A: cholesterol acyltransferase-inhibitory effective amount of a compound as defined by claim 1 in combination with a pharmceutically acceptable carrier.

25. A method of inhibiting intestinal absorption of cholesterol in mammals comprising administering to said mammal an acyl-coenzyme A: cholesterol acyltransferase-inhibitory effective amount of a compound as defined by claim 1 in combination with a pharmaceutically acceptable carrier.

* * * * *